(12) United States Patent
Taoka et al.

(10) Patent No.: US 7,676,024 B2
(45) Date of Patent: Mar. 9, 2010

(54) X-RAY IMAGING DEVICE

(75) Inventors: Akira Taoka, Hamamatsu (JP); Kazuhisa Miyaguchi, Hamamatsu (JP)

(73) Assignee: Hamamatsu Photonics K.K., Hamamatsu-shi, Shizuoka (JP)

( * ) Notice: Subject to any disclaimer, the term of this patent is extended or adjusted under 35 U.S.C. 154(b) by 0 days.

(21) Appl. No.: 11/885,766

(22) PCT Filed: Mar. 7, 2006

(86) PCT No.: PCT/JP2006/304308
§ 371 (c)(1),
(2), (4) Date: May 12, 2008

(87) PCT Pub. No.: WO2006/095702
PCT Pub. Date: Sep. 14, 2006

(65) Prior Publication Data
US 2008/0247514 A1 Oct. 9, 2008

(30) Foreign Application Priority Data
Mar. 8, 2005 (JP) .............................. 2005-064352

(51) Int. Cl.
*H05G 1/30* (2006.01)

(52) U.S. Cl. ..................................... 378/98.8; 378/189

(58) Field of Classification Search ................ 378/98.8, 378/114, 115, 116, 191, 98.2, 98
See application file for complete search history.

(56) References Cited

U.S. PATENT DOCUMENTS
2003/0030004 A1* 2/2003 Dixon et al. ............ 250/370.09

FOREIGN PATENT DOCUMENTS
JP 11-502055 2/1999
JP 3335350 8/2002

* cited by examiner

*Primary Examiner*—Hoon Song
(74) *Attorney, Agent, or Firm*—Drinker Biddle & Reath LLP

(57) ABSTRACT

An apparatus includes: an imaging unit 7, an X-ray detecting unit 90, outputting, upon irradiation of X-rays, an X-ray detection signal over the irradiation period; an operation controlling unit 13, generating a trigger indicating an imaging start timing based on the X-ray detection signal and using the trigger to perform operation controlling of the imaging unit 7; and a signal cable L1, containing, within a tube 11, one or a plurality of each of a detection signal line L11, transmitting the X-ray detection signal, a controlling signal line L12, transmitting a controlling signal for drive control of the imaging unit 7, and an image signal line L13, transmitting image signals, resulting from imaging by the imaging unit 7, and in the signal cable L1, the detection signal line L11 is disposed at an inner central portion of the tube 11 and the other signal lines are disposed so as to surround the detection signal line L11. The occurrence of malfunctions in the X-ray imaging apparatus is thereby reduced.

2 Claims, 6 Drawing Sheets

(a)

(b)

(a)

(b)

X-RAY IMAGING DEVICE

TECHNICAL FIELD

The present invention relates to an X-ray imaging apparatus for taking X-ray images.

BACKGROUND ART

X-ray imaging systems that use a CCD (charge coupled device) to take an X-ray image have recently come to be used widely in medical fields, etc. Such an X-ray imaging system has an X-ray irradiating apparatus that irradiates X-rays and an X-ray imaging apparatus that takes an X-ray image resulting from the X-ray irradiation. The X-ray imaging apparatus has an imaging unit, having a CCD for taking the X-ray image, an X-ray detecting unit for detecting whether or not X-ray irradiation is being performed, and an operation controlling unit for controlling the operation of the imaging unit and the X-ray detecting unit. The X-ray detecting unit is a photodiode, etc., that photoelectrically converts the irradiated X-rays and outputs an X-ray detection signal. The operation controlling unit detects, on the basis of the detection signal output from the X-ray detecting unit, a start timing (or, further, an end timing) of an entire X-ray irradiation period for each single time of X-ray imaging (referred to hereinafter simply as the "entire X-ray irradiation period") and, based on the detected timing, generates a trigger that indicates an imaging start timing (or, further, an imaging end timing). Based on this trigger, the operation controlling unit performs operation controlling of the CCD to perform X-ray imaging.

When such an X-ray imaging system is arranged, for example, for imaging an X-ray image of teeth of a subject, the imaging unit and the X-ray detecting unit have dimensions and shapes enabling insertion inside a mouth of the subject and are used in a state of being inserted inside the mouth during X-ray imaging. In the X-ray imaging process, the operation controlling unit is connected, via a signal cable that enables the sending and receiving of various signals (controlling signals and image signals), to the imaging unit and the X-ray detecting unit, which are inserted in the mouth of the subject, and is disposed and used outside the subject in this state. The signal cable contains, for example, a signal line that transmits the X-ray detection signal, for generating the trigger that indicates the imaging start timing, from the X-ray detecting unit to the operation controlling unit.

Patent Document 1: Japanese Translation of PCT International Application No. H11-502055
Patent Document 2: Japanese Patent No. 3335350

DISCLOSURE OF THE INVENTION

Problems to be Solved by the Invention

The above-described signal cable is a multicore cable with a diameter of approximately 3 mm and a length of approximately 2 m and has a dozen or so thin cables bundled therein, and impact due to various causes such as sudden bending, dropping, etc., is readily applied thereto. When an impact is applied to the signal cable, a physical stress is applied to the signal lines themselves and in accompaniment with the stress, electrical noise is generated. When the electrical noise becomes a signal and is transmitted via the signal line to the operation controlling unit, the operation controlling unit processes this signal due to electrical noise as the X-ray detection signal output from the X-ray detecting unit. In this case, even though X-ray irradiation is not actually performed, a malfunction in the imaging operation may occur in which the trigger indicating the imaging start timing is generated and imaging is performed erroneously. In particular, such an impact is received more readily and electrical noise is generated in the signal line more readily the longer the cable and when the signal line is positioned at an outer side of the cable. Malfunctions correspondingly occur more readily in such cases.

An object of the present invention is thus to reduce the occurrence of malfunctions in the X-ray imaging apparatus.

Means for Solving the Problems

An X-ray imaging apparatus according to the present invention includes: an imaging unit, taking an X-ray image obtained by X-ray irradiation; an X-ray detecting unit, outputting, when X-rays are irradiated, an X-ray detection signal over an irradiation period; an operation controlling unit, generating a trigger indicating an imaging start timing for an X-ray image based on the X-ray detection signal and using the trigger to perform drive control of the imaging unit; and a signal cable, containing, within a tube, one or a plurality of each of a detection signal line, transmitting the X-ray detection signal from the X-ray detecting unit to the operation controlling unit, a controlling signal line, transmitting a controlling signal for operation controlling of the imaging unit from the operation controlling unit to the imaging unit, and an image signal line, transmitting image signals, resulting from imaging by the imaging unit, from the imaging unit to the operation controlling unit, and in the signal cable, the detection signal line is disposed so as to be surrounded by any of the other signal lines among the three signal lines.

With the present invention, the detection signal line that transmits the X-ray detection signal for generating the trigger indicating the imaging start timing is positioned so as to be surrounded by any of the other signal lines. Thus, even if an impact, due to dropping, sudden bending, etc., is applied to the signal cable itself, in regard to the detection signal line, such an impact is relaxed by the presence of the other signal cables positioned outside the detection signal line. Because noise due to impact is thus made less likely to occur in the detection signal line, a malfunction, in which the trigger indicating the imaging start timing is generated erroneously due to noise, can be suppressed reliably.

EFFECTS OF THE INVENTION

By the present invention, the occurrence of malfunctions in the imaging operation in the X-ray imaging apparatus can be reduced.

DESCRIPTION OF THE SYMBOLS

1—X-ray irradiating apparatus, 2—X-ray imaging apparatus, 3—PC, 4—display, 5—optical image acquiring unit, 6—controlling unit, 7—imaging unit, 8—connecting unit, 9—trigger generating unit, 10—X-ray imaging system, 11—tube, 12—holding member, 13—operation controlling unit, 61—signal processor, 62—trigger processor, 63—I/O controller, 64—A/D converter, 65—CCD driver, 71—scintillator, 72—CCD, 73—CCD controller, 81—connector, 90—X-ray detecting unit, 91—PD, 92—amplifier, 92a—I-V converting amplifier, 92b—gain amplifier, 93—trigger generator, 93a—comparator, 93c—time-constant-determining C, R connection, 93d—NOR circuit, 93b—monostable multivibrator, L1—signal cable, L11—detection signal line, L12—controlling signal line, L13—image signal line, L14—GND line, L2—signal cable.

BEST MODES FOR CARRYING OUT THE INVENTION

A preferred embodiment of an X-ray imaging apparatus according to the present invention shall now be described in detail with reference to the drawings. In the description of the drawings, elements that are the same shall be provided with the same symbols and overlapping description shall be omitted.

Figure 1:
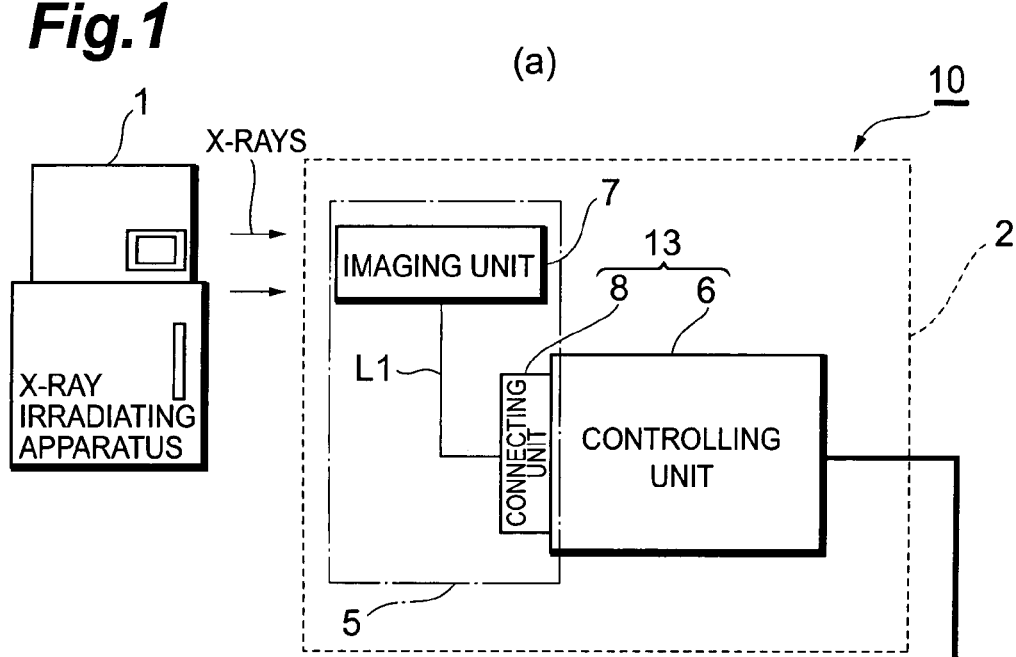
FIG. 1 shows a block diagram of an arrangement of an X-ray imaging system according to an embodiment.
Figure 1:
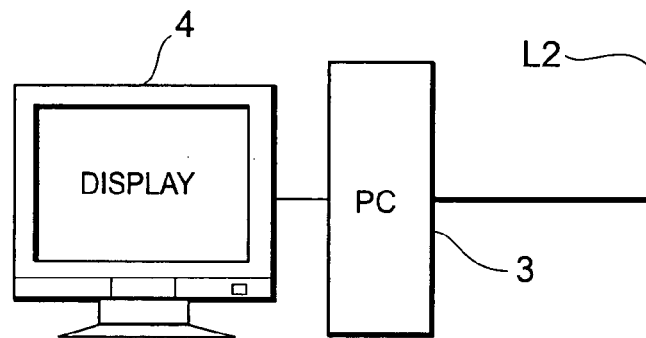
Figure 1:
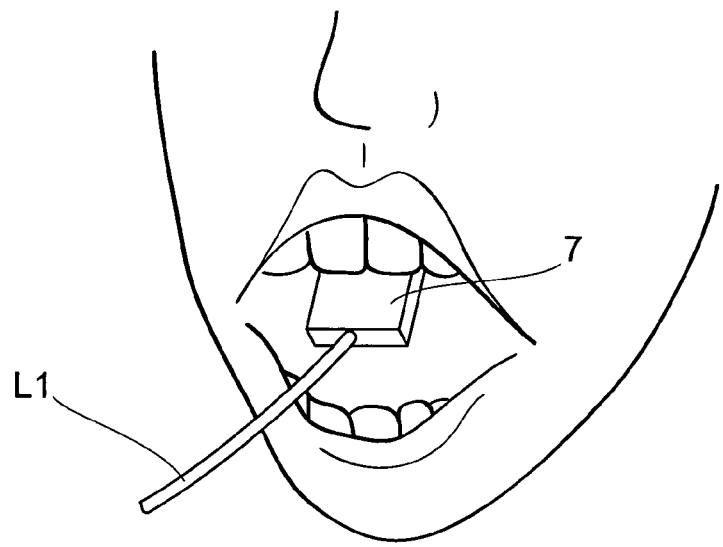

First, the arrangement of an X-ray imaging system 10 shall be described with reference to (a) in FIG. 1. The X-ray imaging system 10 is a medical-use X-ray imaging system for performing X-ray imaging of teeth, etc., of a subject. The X-ray imaging system 10 has an X-ray irradiating apparatus 1, an X-ray imaging apparatus 2, a PC (personal computer) 3, and a display 4.

The X-ray irradiating apparatus 1 is an X-ray irradiating apparatus for irradiating X-rays onto teeth, etc., and is arranged as a fixed installation type apparatus. In response to an X-ray irradiation start instruction, the X-ray irradiating apparatus 1 performs stationary X-ray irradiation in accordance with a voltage waveform of a complete DC voltage obtained by a high-frequency inverter method until an X-ray irradiation end instruction is input (or until expiration of an irradiation end timer). The X-ray irradiating apparatus 1 can also perform cyclic X-ray irradiation according to a half-wave rectified waveform of an AC power supply voltage.

The X-ray imaging apparatus 2 is an X-ray imaging apparatus for taking an X-ray image of teeth, etc., and has an optical image acquiring unit 5 and a controlling unit 6. The optical image acquiring unit 5 has an imaging unit 7 and a connecting unit 8 that are connected to each other via a signal cable L1. The controlling unit 6 and the connecting unit 8, having a trigger generator 93, to be described below, constitute an operation controlling unit 13 (operation controller) for operation controlling of the imaging unit 7.

The imaging unit 7 has a CCD 72 to be described below and takes an X-ray image of teeth, etc., by means of the CCD 72. The imaging unit 7 has dimensions and a shape that enable easy insertion into an oral cavity of a subject. An example of a state in which the imaging unit 7 is inserted in an oral cavity of a subject is shown in (b) in FIG. 1. The imaging unit 7 is inserted into an inner side of front teeth of an upper jaw of the subject, and the signal cable L1 extends from the imaging unit 7 to the exterior of the oral cavity.

The signal cable L1 has a shape and dimensions of a long, thin form and is a multicore cable with a diameter of approximately 3 mm, in which a dozen or so thin cables are bundled together. In the signal cable L1, one or a plurality of cables of each of signal lines L11 to L13, that is, a detection signal line L11, a controlling signal line L12, and an image signal line L13 (see (a) in FIG. 2 and FIG. 3), all of which have excellent flexibility, are contained inside a tube 11, constituted of an outer sheath of a material of excellent flexibility, such as PVC or fluororesin, that can adequately lighten discomfort and pain inflicted on the subject in the state in which the imaging unit 7 is inserted in the oral cavity of the subject (see (b) in FIG. 1).

Figure 2:
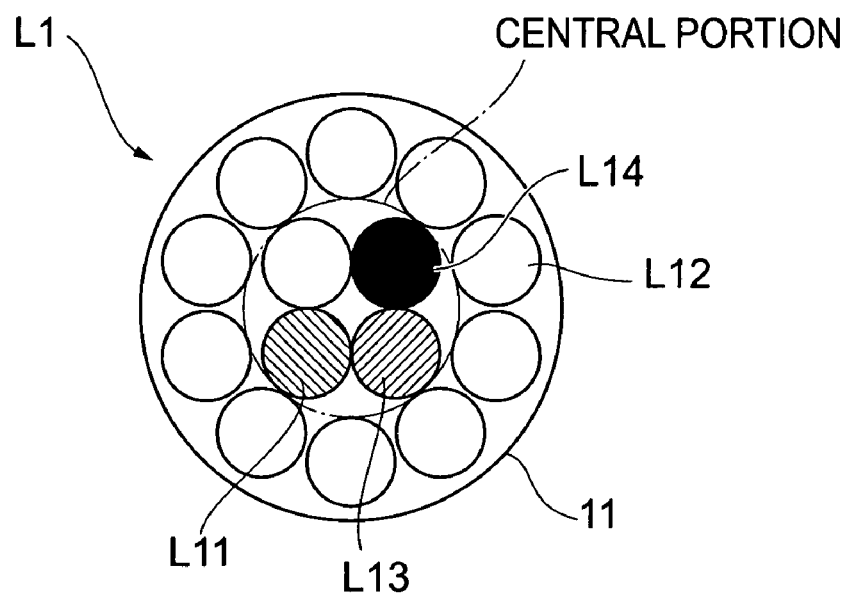
FIG. 2 shows schematic diagrams of a cross-sectional arrangement of an interior of a signal cable of the embodiment.
Figure 2:
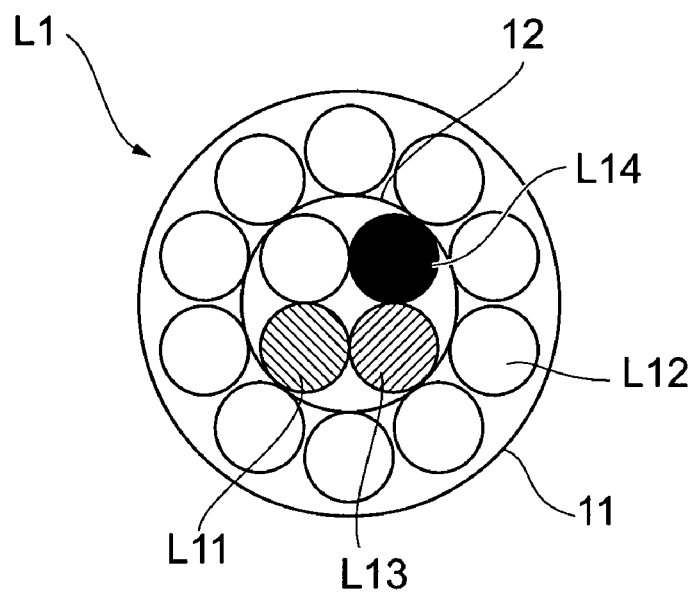

Here, as shown in (a) in FIG. 2, the signal cable L1 contains one each of the detection signal line L11 and the image signal line L13, eleven controlling signal lines L12, and a single GND (ground) line L14. The single detection signal line L11 and the single image signal line L13 are disposed, along with the single GND line L14 and a single controlling signal line L12, at the inner side of the signal cable L1, and ten controlling signal lines L12 are disposed at the outer side of these lines.

The details of the positions and the numbers of the signal lines L11 to L13 in the signal cable L1 are not restricted to those shown in (a) in FIG. 2 as long as these are as described above. For example, as shown in (b) in FIG. 2, the signal cable L1 may have a holding member 12, extending in a longitudinal direction of the tube 11, at the inner side of the tube 11, one each of the detection signal line L11, controlling signal line L12, image signal line L13, and GND line L14 may be positioned at the inner side of the holding member 12, and ten controlling signal lines L12 may be positioned at the outer side of the holding member 12. In this case, the holding member 12 is formed of paper or other material of excellent flexibility as is the tube 11. The holding member 12 may also be an arrangement, with which the detection signal line L11, controlling signal line L12, image signal line L13, and GND line L14 are bundled together by a tape-like member.

The controlling unit 6 is connected via a signal cable L2 to the PC 3. The controlling unit 6 controls the optical image acquiring unit 5 (in particular, the imaging unit 7) and transmits image data to the PC 3 in accordance with various control instructions for the optical image acquiring unit 5 that are transmitted from the PC 3. As a recent example of the signal cable L2, a USB (universal serial bus) cable, etc., can be used, and with a USB cable, in addition to the sending and receiving of signals, power can be supplied to the X-ray imaging apparatus 2 as well.

The PC 3 sets various parameters (for example, sets the resolution) in and instructs X-ray imaging to the X-ray imaging apparatus 2 via the signal cable L2, takes in image data, expressing an X-ray image, from the X-ray imaging apparatus 2, performs various analysis (for example, extraction, magnification, etc., of a specific region of an image), and stores the image data and data expressing the analysis results in a memory. Furthermore, the PC 3 displays an X-ray image on the display 4 based on the image data taken in from the X-ray imaging apparatus 2 and displays the analysis results, etc., concerning the image data. Here, the display 4 has a display unit, such as a CRT (cathode ray tube), an LCD (liquid crystal display), etc.

Figure 3:
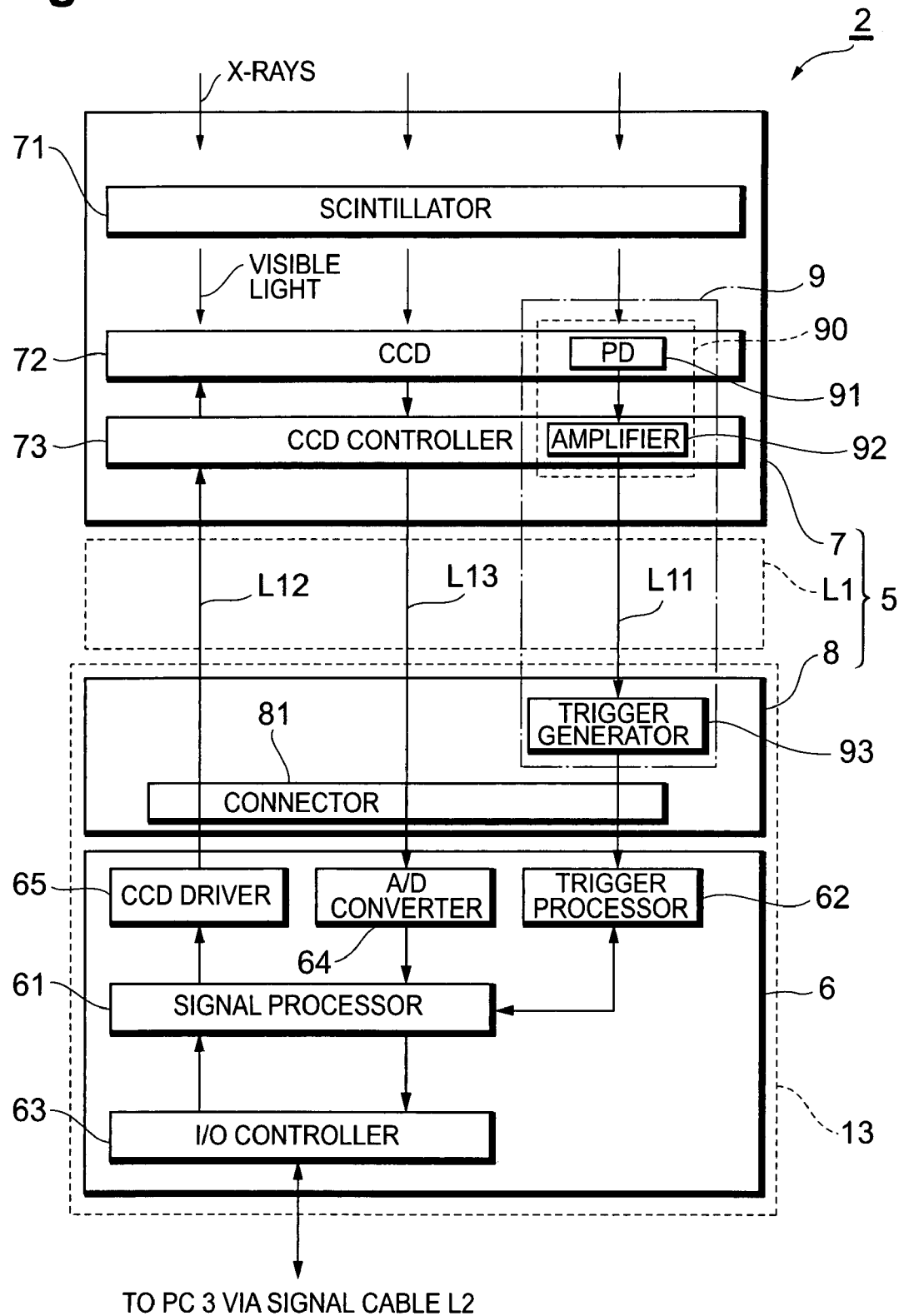
FIG. 3 is a block diagram of an arrangement of an X-ray imaging apparatus according to the embodiment.

An arrangement of the X-ray imaging apparatus 2 shall now be described in detail with reference to FIG. 3. The imaging unit 7 has a scintillator 71, a CCD 72, and a CCD controller 73. When X-rays are made incident thereon, the scintillator 71 emits visible light of a light amount corresponding to the energy amount of the X-rays. Upon illumination of the visible light from the scintillator 71, the CCD 72 performs photoelectric conversion of the visible light, generates charges corresponding to the light amount of the visible light (charges expressing an image), and accumulates the charges in a readable manner (this process shall also be referred to hereinafter as "imaging"). Upon receiving a controlling signal for the CCD 72 from the controlling unit 6, the CCD controller 73 drives and controls the CCD 72 in accordance with the controlling signal. Here, the controlling signal for the CCD 72 is, for example, an imaging instruction of an X-ray image, a read instruction, etc. In the description that follows, "signal" shall refer to an analog signal.

The connecting unit 8 is for detachably connecting the optical image acquiring unit 5 to the controlling unit 6 and has a connector 81. The connector 81 is, for example, a 36-pin MDR connector, etc. The controlling signal for the imaging unit 7 by the controlling unit 6 is transmitted from the controlling unit 6 to the imaging unit 7 via the connecting unit 8 and the signal cable L1 (controlling signal line L12). Image signals expressing the X-ray image taken by the imaging unit 7 are transmitted to the controlling unit 6 via the connecting unit 8 and the signal cable L1 (image signal line L13).

The optical image acquiring unit 5 has a trigger generating unit 9. The trigger generating unit 9 generates trigger signals for the imaging unit 7 that express an imaging start instruction and an imaging end instruction for an X-ray image and outputs these trigger signals to the controlling unit 6. The trigger generating unit 9 has an X-ray detecting unit 90 having a PD (photodiode) 91 and an amplifier 92, and a trigger generator 93 that is connected to the X-ray detecting unit 90 via the signal cable L1 (detection signal line L11).

The controlling unit 6 has a signal processor 61, a trigger processor 62, an I/O controller 63, an A/D converter 64, and a CCD driver 65. The controlling unit 6 has a connecting terminal, to and from which the connector 81 of the optical image acquiring unit 5 can be attached and detached, and the sending and receiving of various signals to and from the optical image acquiring unit 5 are performed via this connecting terminal. The controlling unit 6 also performs the sending and receiving of various data to and from the PC 3 via the signal cable L2. In the description that follows, "data" shall refer to digital data.

In accordance with trigger data (data indicating an imaging start timing and an imaging end timing for an X-ray image), which shall be described below and are input from the trigger processor 62, and command data, which are input from the PC 3 via the I/O controller 63, the signal processor 61 generates control data for the optical image acquiring unit 5 (or the trigger processor 62 or other component) or takes in image data from the optical image acquiring unit 5 via the A/D converter 64 and transmits the image data via the I/O controller 63 to the PC 3 side.

As shall be described in detail below, if, after detecting a falling edge (start) timing of a below-described trigger signal pulse (a Low signal pulse P4 or P8 of a trigger signal S6, shown in FIG. 5) input from the trigger generating unit 9 (that is, upon detecting a start timing of an entire X-ray irradiation period T1, shown in FIG. 5), a rising edge (end) of the pulse does not occur within an elapse, from the falling edge timing, of a period slightly longer than a pulse width (pulse width W, shown in FIG. 5) of a pulse generated by a monostable multivibrator 93*b*, the trigger processor 62 outputs, at the timing of elapse, the trigger data, indicating the imaging start timing, to the signal processor 61. Thus, even if a single isolated signal of short pulse width that is due to noise is input into the trigger processor 62, a malfunction, in which the trigger data indicating the imaging start timing is output erroneously, can be avoided. Furthermore, upon detecting a rising edge timing of the trigger signal pulse input from the trigger generating unit 9 (an end timing of the entire X-ray irradiation period T1, shown in FIG. 5), the trigger processor 62 outputs, at the rising edge timing, the trigger data, indicating the imaging end timing, to the signal processor 61.

The I/O controller 63 has an interface for performing the sending and receiving of data to and from the PC 3 via the signal cable L2 based on a data transmission method such as USB, IEEE 1394, etc. The I/O controller 63 is not restricted to wired data transmission and may instead have an interface corresponding to a wireless data transmission method, such as wireless LAN (local area network), Bluetooth, etc.

The A/D converter 64 converts image signals taken in from the imaging unit 7 into image data and outputs the data to the signal processor 61. The CCD driver 65 generates controlling signals (signal pulses) according to various control data for the optical image acquiring unit 5 that are input from the signal processor 61 and outputs the controlling signals to the optical image acquiring unit 5.

The above-described functions of the signal processor 61 may be realized by hardware or may be realized by software.

Figure 4:
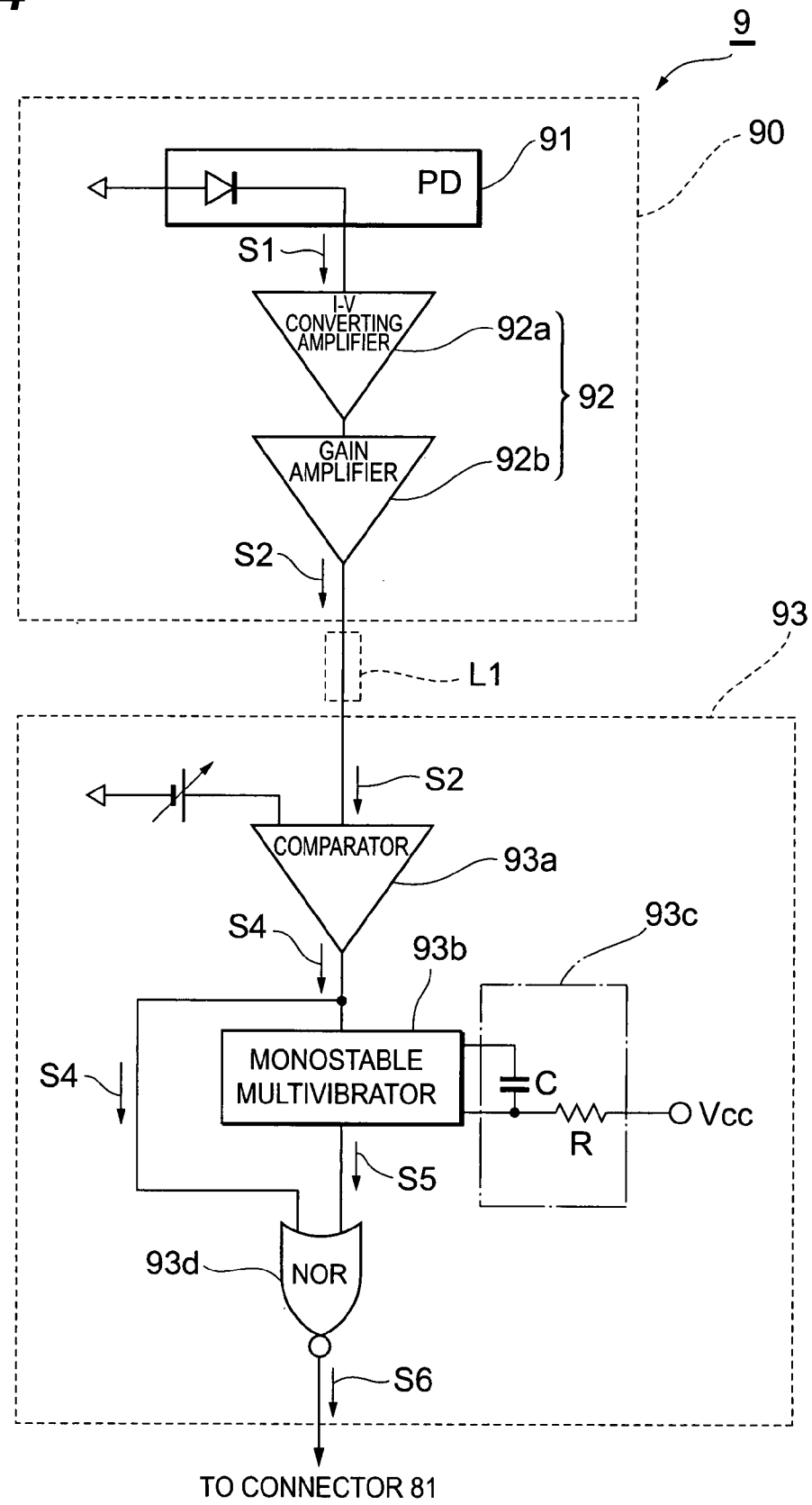
FIG. 4 is a block diagram of an arrangement of a trigger generating unit of the embodiment.

An arrangement and operation of the trigger generating unit 9 shall now be described in detail with reference to FIGS. 4 and 5.

The PD 91 detects X-rays irradiated by the X-ray irradiating apparatus 1. Here, the X-ray irradiation is stationary in accordance with the voltage waveform of the complete DC voltage obtained by the high-frequency inverter method in the X-ray irradiating apparatus 1. The PD 91 outputs an electrical signal (referred to hereinafter as "signal S1") in accordance with the energy amount of the detected X-rays. The signal S1 thus contains a pulse P1 with a pulse width corresponding to the entire X-ray irradiation period T1 (approximately a few dozen msec to few seconds).

The amplifier 92 has an I-V converting amplifier 92*a* and a gain amplifier 92*b*. At the amplifier 92, the I-V converting amplifier 92*a* converts the signal S1, input from the PD 91, from a current value to a voltage value, and further the gain amplifier 92*b* amplifies the signal S1, which has been converted to the voltage value, to a signal level enabling processing by the connecting unit 8 at the subsequent stage and outputs the amplified signal as a signal S2 (X-ray detection signal). The amplifier 92 outputs the signal S2 to the trigger generator 93 via the signal cable L1 (detection signal line L11).

The trigger generator 93 has a comparator 93*a*, the monostable multivibrator 93*b*, a time-constant-determining C, R connection 93*c*, and a NOR circuit 93*d*.

When the signal S2, input from the amplifier 92 via the signal cable L1 (detection signal line L11), is no less than a reference signal level S3, the comparator 93*a* outputs a signal S4 to the monostable multivibrator 93*b* and the NOR circuit 93*d*. The signal S4 contains a pulse P2 with a pulse width corresponding to a time width during which the signal S2 is no less than the reference signal level S3 (time width substantially equal to the entire X-ray irradiation period T1).

When the signal S4 from the comparator 93*a* is input, the monostable multivibrator 93*b* outputs, in synchronization with the rising edge (start) of the pulse P2, contained in the signal S4, a pulse P3 (signal S5) to the NOR circuit 93*d*. Here, the pulse P3 has a pulse width W (20 to 40 msec) that is determined by the respective values of a capacitance C and a resistance R, included in the time-constant-determining C, R connection 93*c*.

If the pulse P3 is contained in the signal S5 or the pulse P2 is contained in the signal S4, the NOR circuit 93*d* outputs a Low signal during a period in which either state continues, and in the other case, that is, if the pulse P3 is not contained in the signal S5 and the pulse P2 is not contained in the signal S4, the NOR circuit 93d outputs a High signal during a period in which this state continues.

The NOR circuit 93d thus outputs the trigger signal S6 that contains the Low signal pulse P4, with a pulse width corresponding to the entire X-ray irradiation period T1, during the entire X-ray irradiation period T1.

For cyclic X-ray irradiation in accordance with a half-wave rectified waveform of an AC power supply voltage, the X-ray imaging apparatus 2 can output the same trigger signal S6 as that in the above-described case of stationary X-ray irradiation. An operation, in which the trigger generating unit 9 outputs the trigger signal S6 when the X-ray irradiation by the X-ray irradiating apparatus 1 is cyclic at a cycle of 50 Hz or 60 Hz in accordance with a half-wave rectified waveform of an AC power supply voltage, shall now be described.

Figure 5:
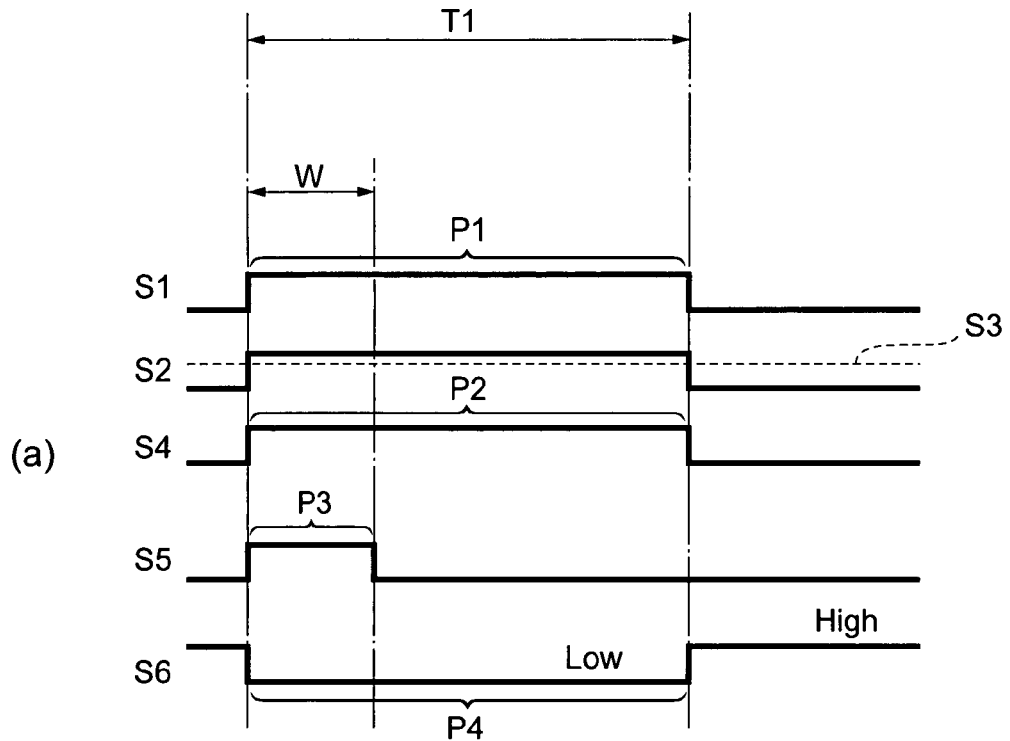
FIG. 5 shows timing charts for describing an operation of the trigger generating unit of the embodiment.
Figure 5:
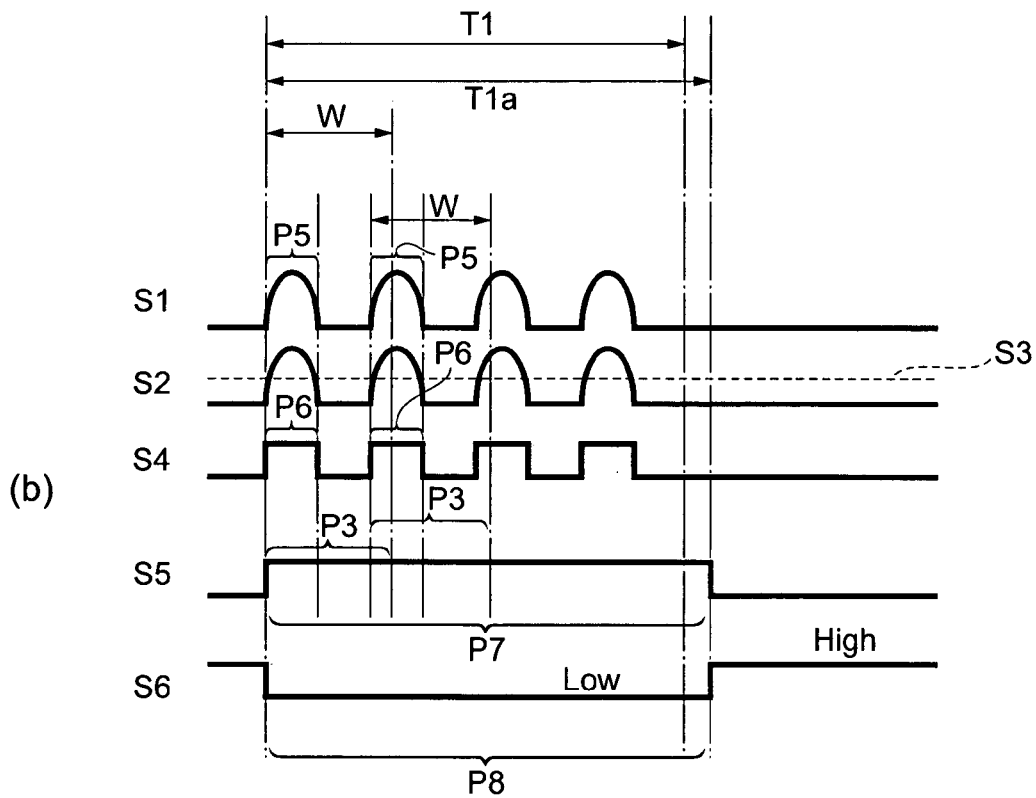

In this case, the signal S2 (and likewise the signal S1), input into the trigger generator 93 from the X-ray detecting unit 90, contains a plurality of pulses P5 in a cyclic manner as shown in (b) in FIG. 5. The signal S4 also contains a plurality of pulses P6 in a cyclic manner in accordance with the pulses P5 (signals S1 and S2).

When a pulse P6 is input, the monostable multivibrator 93b outputs the pulse P3 with the pulse width W. When during this output of the pulse P3, a pulse P6 is input anew, the monostable multivibrator 93b outputs the pulse P3 anew in synchronization with the rising edge (start) of the newly input pulse P6. Thus, at the monostable multivibrator 93b, as long as the pulse P6 is input during the output of the pulse P3, the pulse width of the signal S5 continues to be extended beyond the pulse width W of the pulse P3. A pulse P7 (signal S5), having a pulse width T1a that is slightly longer than a period (entire X-ray irradiation period T1), in which the signal S1 contains the pulses P5 in a cyclic and continuous manner, is thereby output.

Here, if the pulse P7 is contained in the signal S5 or the pulse P6 is contained in the signal S4, the NOR circuit 93d outputs a Low signal during a period in which either state continues, and in the other case, that is if the pulse P7 is not contained in the signal S5 and the pulse P6 is not contained in the signal S4, the NOR circuit 93d outputs a High signal during a period in which this state continues.

The NOR circuit 93d thus outputs the trigger signal S6 that contains the Low signal pulse P8, with the pulse width T1a substantially corresponding to the entire X-ray irradiation period T1, during the entire X-ray irradiation period T1.

Thus, regardless of whether the X-ray irradiation by the X-ray irradiating apparatus 1 takes on the form of a stationary pulse of wide width in accordance with the voltage waveform of the complete DC voltage obtained by the high-frequency inverter method in the X-ray irradiating apparatus 1 or takes on the form of cyclic pulses of narrow width in accordance with the half-wave rectified waveform of the AC power supply voltage, the trigger generating unit 9 outputs the trigger signal S6 that contains the Low signal pulse P4 or P8 with a pulse width corresponding to the entire X-ray radiating period T1 in likewise manner in both cases.

An operation of an X-ray imaging apparatus shall now be described with reference to FIG. 6. Upon input of the trigger signal S6 from the trigger generating unit 9, the trigger processor 62 outputs, to the signal processor 61, the trigger data that indicates the imaging start timing for the X-ray image and the trigger data that indicates the imaging end timing.

If upon detecting the falling edge (start) timing of the Low signal pulse P4 (or P8), the rising edge of the Low signal pulse P4 does not occur until an elapse, from the falling edge timing, of a period slightly longer than the pulse width W, the trigger processor 62 outputs, at the timing of elapse, the trigger data, indicating the imaging start timing, to the signal processor 61. A malfunction, in which the trigger data indicating the imaging start timing is output erroneously due to noise, can thereby be avoided.

Figure 6:
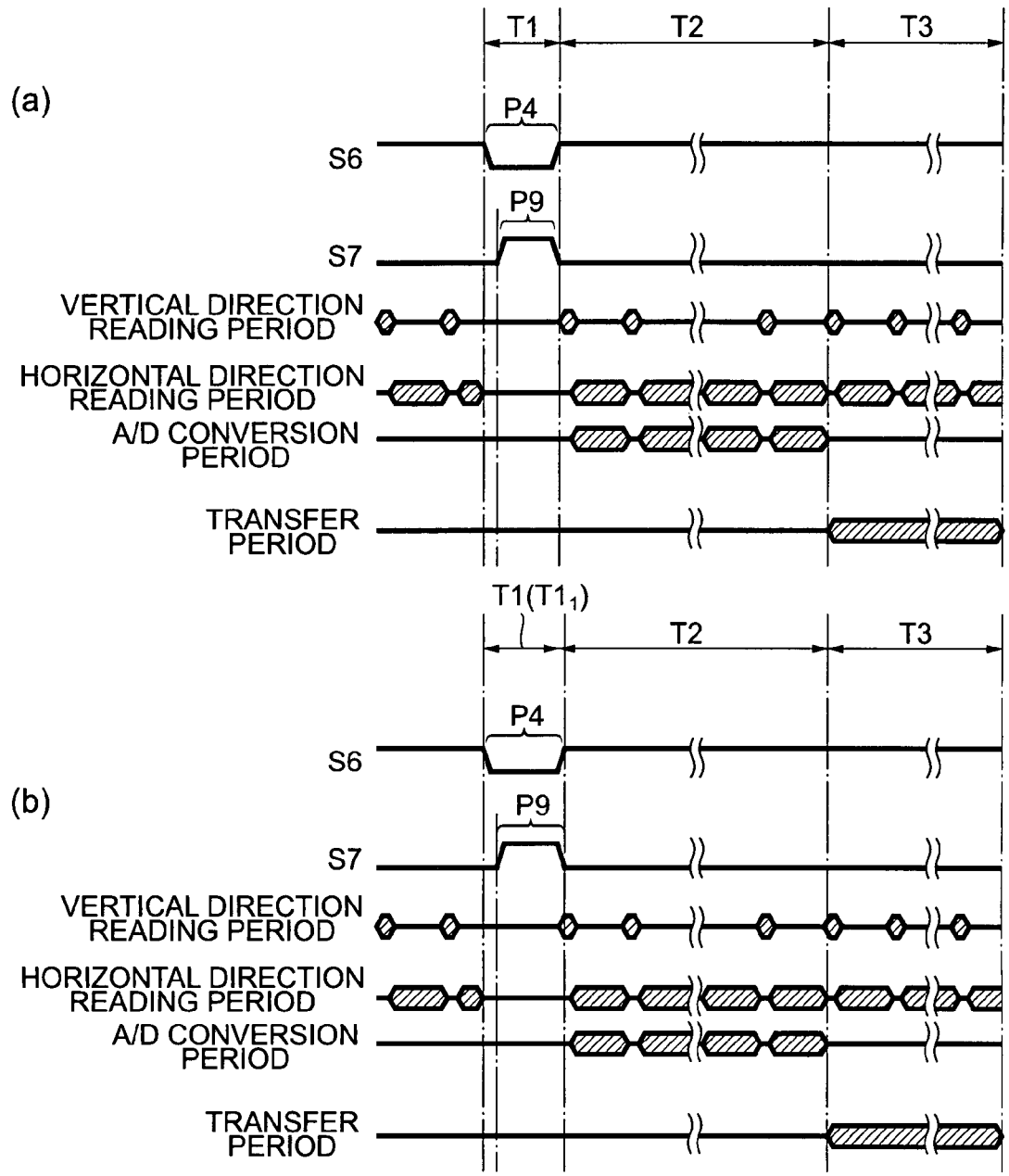
FIG. 6 shows timing charts for describing an operation of the X-ray imaging apparatus according to the embodiment.

Then, upon actually detecting the rising edge (end) timing of the Low signal pulse P4 (or P8), the trigger processor 62 outputs the trigger data indicating the imaging end timing to the signal processor 61 at the rising edge timing as shown in (a) in FIG. 6 (first imaging mode).

The signal processor 61 may, as shown in (b) in FIG. 6, output the trigger data indicating the imaging end timing to the signal processor 61 at a timing at which a predetermined period $T1_1$ (a period that is preset in correspondence to the entire X-ray irradiation period T1) just elapses from the falling edge (start) timing of the Low pulse P4 (second imaging mode).

Based on command data transmitted from the PC 3 via the signal processor 61, the trigger processor 62 sets in which of the first and second imaging modes the X-ray imaging is to be performed. The imaging end timing in the second imaging mode may be arranged to be detected not by the trigger processor 62 but by the signal processor 61 instead.

The signal processor 61 makes the CCD driver 65 output, to the imaging unit 7, a pulse P9 (controlling signal S7) with a pulse width corresponding to a period from the input of the trigger data indicating the imaging start timing to the input of the trigger data indicating the imaging end timing under the first imaging mode (or the period until the imaging end timing under the second imaging mode).

Here, the rising edge (start) timing of the pulse P9 is delayed from the start timing of the entire X-ray irradiation period T1 by a period that slightly exceeds the pulse width W. This is because, as described above, in order to prevent malfunctions due to noise, the output of the trigger data indicating the imaging start timing at the trigger processor 62 is delayed from the start timing of the entire X-ray irradiation period T1. The imaging unit 7 then starts imaging (accumulation of image signals) in synchronization with the rising edge (start) timing of the pulse P9 and ends imaging (accumulation of image signals) in synchronization with the falling edge (end) timing of the pulse P9 (period T1).

Then, after the end of imaging, the image signals accumulated by the imaging unit 7 during the imaging period are read by the signal processor 61 (period T2). Here, the signal processor 61 makes the CCD controller 73 of the imaging unit 7 read horizontal component and vertical component image signals alternately from the CCD 72 in accordance with the resolution designated by the PC 3, etc., in advance. The image signals read from the imaging unit 7 are successively converted into image data at the A/D converter 64 and are taken into the signal processor 61.

After the period T2, the signal processor 61 successively transfers the image data, taken in via the A/D converter 64, to the PC 3 via the I/O controller 63 (period T3).

As described above, with the X-ray imaging apparatus 2 according to the present embodiment, regardless of whether the X-ray irradiation by the X-ray irradiating apparatus 1 takes on the form of a stationary pulse of wide width in accordance with the voltage waveform of a complete DC voltage obtained by the high-frequency inverter method in the X-ray irradiating apparatus 1 or takes on the form of cyclic pulses of narrow width in accordance with the half-wave rectified waveform of the AC power supply voltage, the trigger indicating the imaging start timing for an X-ray image and the trigger indicating the imaging end timing can be output appropriately while preventing malfunctions in the imaging operation due to noise in likewise manner in both cases. Taking of a good X-ray image is thereby enabled.

Furthermore, the detection signal line L11 that transmits the signal S2 for generating the trigger indicating the imaging start timing (and furthermore, a controlling signal line L12, the image signal line L13, and the GND line L14) are disposed at the inner, central portion of the signal cable L1, and the controlling signal lines L12 are disposed at the outer side thereof. Thus, even when an impact, due to dropping, sudden bending, etc., is applied to the signal cable L1 itself, such an impact can be adequately relaxed, with respect to the detection signal line L11 that is securely disposed at the inner, central portion of the signal cable L1 (in particular, disposed inside the holding member 12), by the presence of the controlling signal lines L12 that are disposed at the outer side of the detection signal line L11. Thus, even when an impact is applied to the signal cable L1, generation of noise due to the impact is unlikely to occur in the detection signal line L11. Malfunctions in the imaging operation, in which noise is generated in the detection signal line L11 and a trigger indicating the imaging start timing is thereby generated erroneously, can thus be suppressed reliably.

The present invention is not restricted to the above-described embodiment, and various modifications are possible. For example, although with the present embodiment, the trigger generator 93 is disposed in the connecting unit 8, the present invention is not restricted thereto, and the trigger generator 93 may instead be disposed in the controlling unit 6. In this case, the signal S2 output from the X-ray detecting unit 90 (amplifier 92) is input, via the signal cable L1 and the connector 81 of the connecting unit 8, into the trigger generator 93, disposed inside the controlling unit 6.

The X-ray imaging apparatus according to the above-described embodiment has an arrangement that includes: the imaging unit, taking an X-ray image obtained by X-ray irradiation; the X-ray detecting unit, outputting, when X-rays are irradiated, the X-ray detection signal over the irradiation period; the operation controlling unit, generating the trigger indicating the imaging start timing for the X-ray image based on the X-ray detection signal and using the trigger to perform operation controlling of the imaging unit; and the signal cable, containing, within the tube, one or a plurality of each of the detection signal line, transmitting the X-ray detection signal from the X-ray detecting unit to the operation controlling unit, the controlling signal line, transmitting the controlling signal for operation controlling of the imaging unit from the operation controlling unit to the imaging unit, and the image signal line, transmitting the image signals, resulting from imaging by the imaging unit, from the imaging unit to the operation controlling unit; and in the signal cable, the detection signal line is disposed so as to be surrounded by any of the other signal lines among the three signal lines.

Preferably with the present X-ray imaging apparatus, the signal cable has the holding member, extending in a longitudinal direction of the tube, at the inner side of the tube, and the detection signal line is held at the inner side of the holding member.

The detection signal line is thus disposed at the inner side of the holding member. Thus, even when an impact is applied to the signal cable due to dropping, sudden bending, etc., such an impact is more reliably relaxed with respect to the detection signal line, and noise due to impact is made even less likely to occur. Malfunctions in the imaging operation, in which noise is generated in the detection signal line and the trigger indicating the imaging start timing is thereby generated erroneously, can thus be suppressed more reliably.

INDUSTRIAL APPLICABILITY

The apparatus of the present invention can be used as an X-ray imaging apparatus with which the occurrence of malfunctions is reduced.

The invention claimed is:

1. An X-ray imaging apparatus comprising:
an imaging unit, taking an X-ray image obtained by X-ray irradiation;
an X-ray detecting unit, including a photodiode which is provided in addition to the imaging unit and outputting, when X-rays are irradiated, an X-ray detection signal over an irradiation period;
an operation controlling unit, generating, based on the X-ray detection signal from the X-ray detecting unit, a trigger indicating an imaging start timing for an X-ray image and using the trigger to perform operation controlling of the imaging unit for taking the X-ray image; and
a signal cable, containing, within a tube, one or a plurality of each of a detection signal line, transmitting the X-ray detection signal from the X-ray detecting unit to the operation controlling unit, a controlling signal line, transmitting a controlling signal for operation controlling of the imaging unit from the operation controlling unit to the imaging unit, and an image signal line, transmitting image signals, resulting from imaging by the imaging unit, from the imaging unit to the operation controlling unit,
wherein in the signal cable, the detection signal line is disposed so as to be surrounded by any of the other signal lines among the detection signal line, the controlling signal line, and the image signal line.

2. The X-ray imaging apparatus according to claim 1, wherein the signal cable has a holding member, extending in a longitudinal direction of the tube, at the inner side of the tube, and the detection signal line is held at the inner side of the holding member.

* * * * *